United States Patent [19]

Celmer et al.

[11] 4,129,578
[45] Dec. 12, 1978

[54] POLYCYCLIC ETHER ANTIBIOTIC

[75] Inventors: Walter D. Celmer, New London; Walter P. Cullen, East Lyme; Mark T. Jefferson, Waterford; Charles E. Moppett, Mystic; John B. Routien, Lyme; Frank C. Sciavolino, East Lyme, all of Conn.

[73] Assignee: Pfizer Inc., New York, N.Y.

[21] Appl. No.: 728,907

[22] Filed: Oct. 1, 1976

Related U.S. Application Data

[63] Continuation of Ser. No. 558,785, Mar. 17, 1975, abandoned, which is a continuation-in-part of Ser. No. 496,289, Aug. 9, 1974, abandoned.

[51] Int. Cl.² .................... C07D 309/22; A61K 31/35

[52] U.S. Cl. .................... 260/345.7 R; 195/80 R; 195/81; 424/283

[58] Field of Search ..................... 260/345.7

[56] References Cited

U.S. PATENT DOCUMENTS 3,812,249   5/1974   Martin et al. ................... 424/121

Primary Examiner—James O. Thomas, Jr.
Assistant Examiner—G. T. Breitenstein
Attorney, Agent, or Firm—Connolly and Hutz

[57] ABSTRACT

A new polycyclic ether antibiotic with anticoccidial, antimicrobial and growth promotant properties, its production by fermentation and methods for its recovery and purification are described.

4 Claims, 4 Drawing Figures

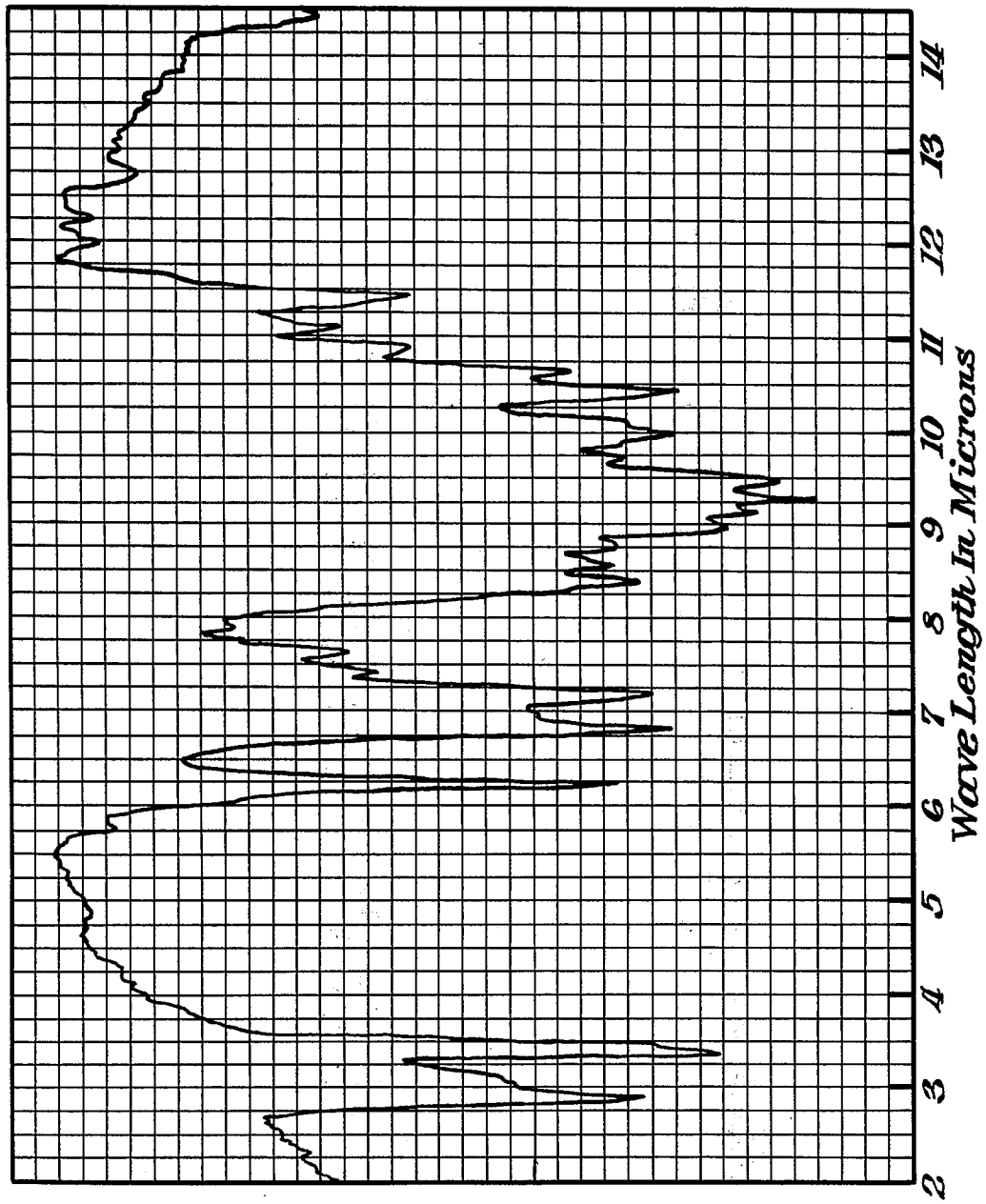
Fig.1. Infrared Absorption Spectrum of Sodium/Potassium Salt of Compound 38,295

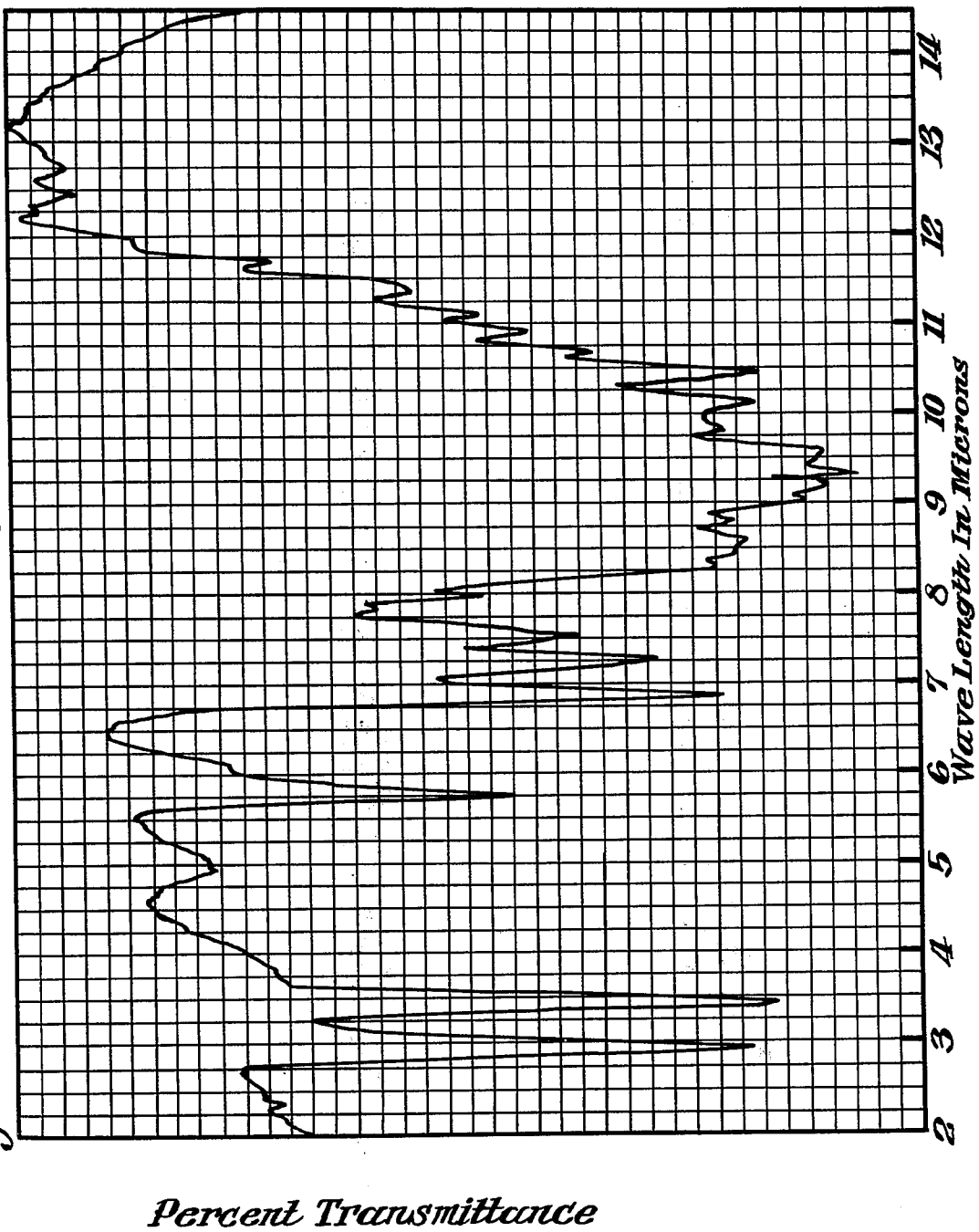

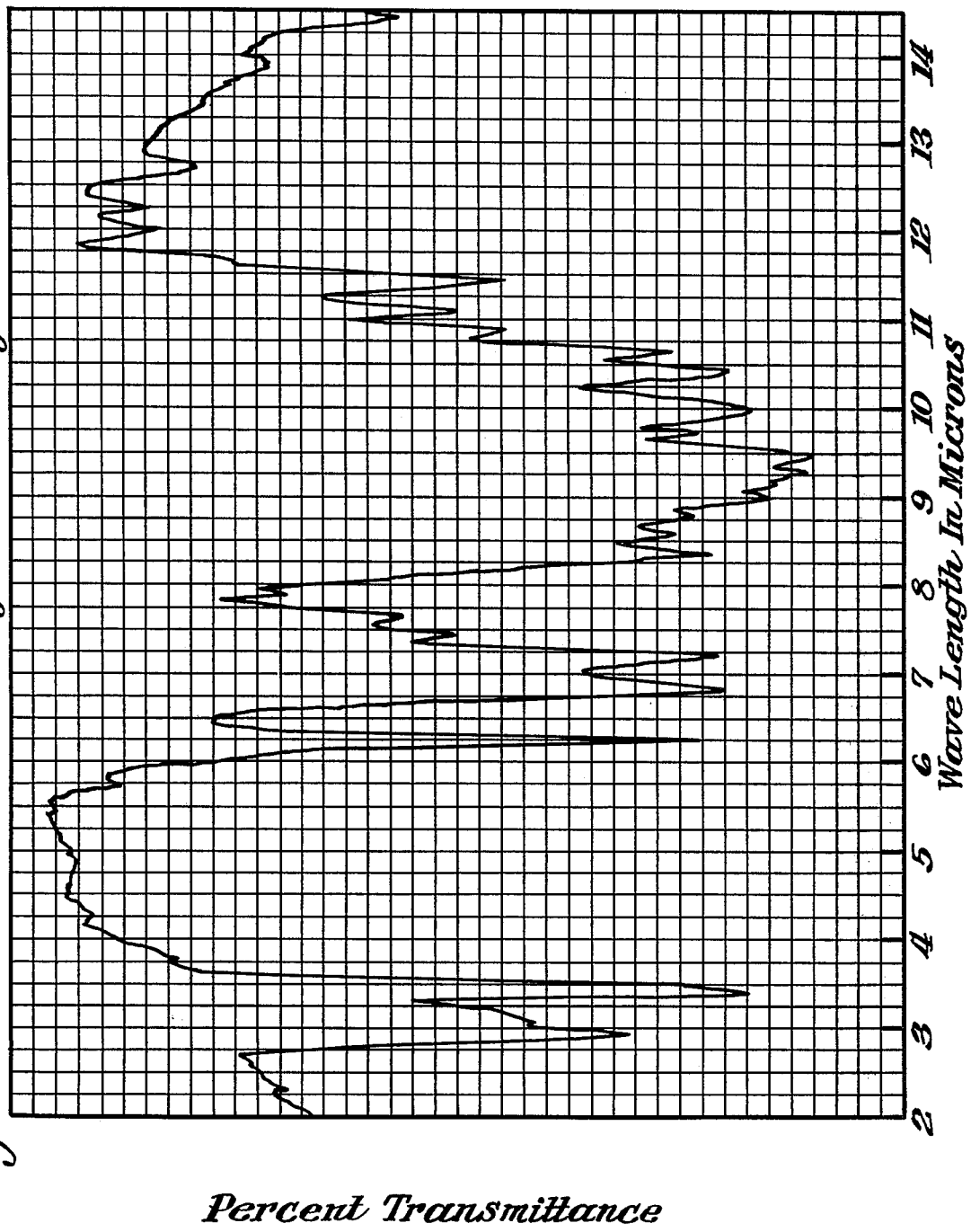

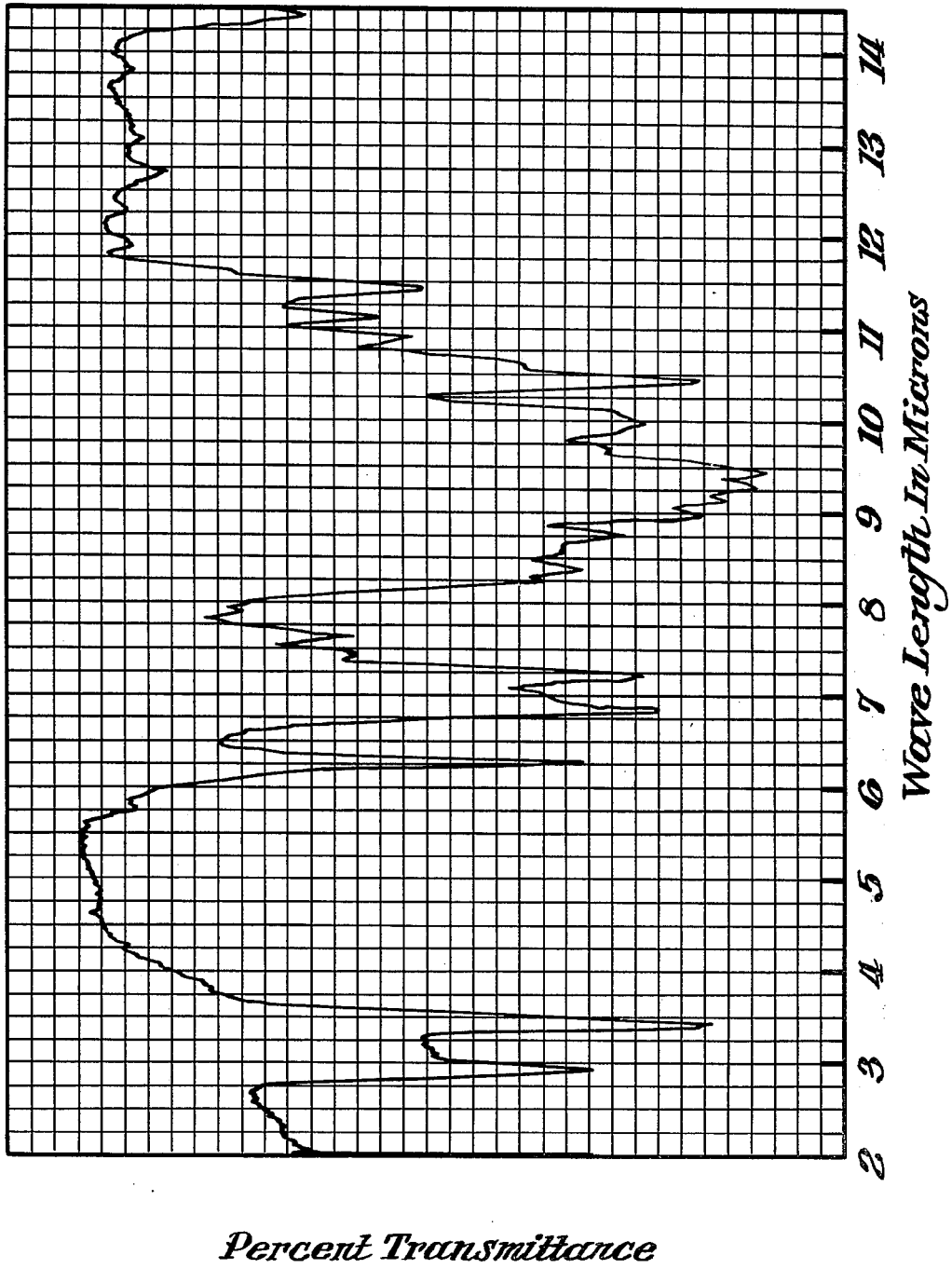

POLYCYCLIC ETHER ANTIBIOTIC

CROSS-REFERENCE TO RELATED APPLICATIONS

This application is a continuation of application Ser. No. 558,785 filed Mar. 17, 1975 now abandoned which is a CIP of application Ser. No. 496,289 filed Aug. 9, 1974 now abandoned.

BACKGROUND OF THE INVENTION

This invention is concerned with a new member of the acidic polycyclic ether group of antibiotics, a class of compounds characterized biologically by their effect on cation transport in mitochondria. This family of antibiotics includes monensin (J. Amer. Chem. Soc., 89:5737, 1967); nigericin (Biochem. Biophys. Res. Comm., 33:29, 1968); grisorixin (J. Chem. Soc. Chem. Commun., 1421, 1970); dianemycin (J. Antibiotics, 22:161, 1969); salinomycin (J. Antibiotics, 27:814, 1974); X-537A (J. Chem. Soc. Chem. Commun., 967, 1972); X-206 (J. Chem. Soc. Chem. Commun., 927, 1971); and A204A (J. Amer. Chem. Soc., 95:3399, 1973).

The polycyclic ether antibiotics listed above are active against Gram-positive bacteria, fungi and protozoa. They exhibit potent anticoccidial activity.

U.S. Pat. No. 3,839,557 describes a process for the improvement of feed utilization by ruminants and monogastric animals fed on fibrous vegetable matter and administered monensin, dianemycin, nigericin or other polycyclic ether antibiotics.

SUMMARY OF THE INVENTION

This invention is concerned with Compound 38,295, an antibiotic having the formula

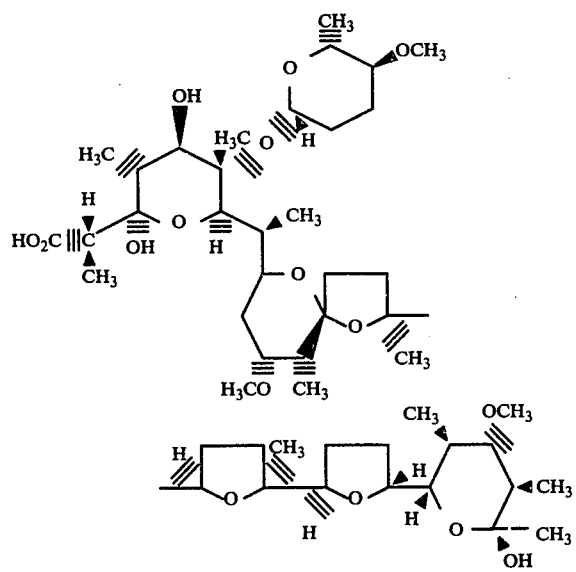

The antibiotic is produced by the submerged aerobic propagation of *Streptomyces hygroscopicus* ATCC 31050 in aqueous nutrient media. The antibiotic and its cationic salts are potent antimicrobial agents and are effective coccidiostats and growth promotants in animals.

DETAILED DESCRIPTION OF THE INVENTION

The microorganism useful for the preparation of the antibiotic of this invention was isolated from a soil sample from Japan. It was grown on a number of media used for the identification of species of this genus and concluded to be quite similar to the description of *Streptomyces hygroscopicus*.

The culture (Pfizer F.D. 23604) was compared in a number of features on several media with a culture of *Streptomyces hygroscopicus* 482.48 obtained from the Dutch public culture collection, Centraalbureau voor Schimmelcultures (CBS). Comparisons and decisions were made on the basis of the concept of the species as described in Applied Microbiology 4:243–250, 1956. A comparison of the two cultures follows:

Spore-chain morphology — chains of Pfizer F.D. 23604 in spirals of 6–10 turns or fewer on different media resembled the described chains of *Streptomyces hygroscopicus* CBS illustrated in FIG. 1 of the paper referred to above. Spores of Pfizer F.D. 23604 examined under the scanning electron microscope looked exactly like those of the CBS strain of *S. hygroscopicus* illustrated in Applied Microbiology, 18:695–696, 1969 where the spores are described as having a rugose surface consisting of numerous pits bordered by ridges of spore wall material. Stained slides of spores of the two cultures looked identical.

Color of colony — aerial mycelium appeared gray on most media but the exact shade was somewhat different for the two cultures. Pfizer F.D. 23604 on Czapek-sucrose agar had a thick, irregularly folded, graying white growth whereas the CBS strain of *S. hygroscopicus* was flat, thin and gray. Pfizer F.D. 23604 on oatmeal agar after four weeks of incubation developed a yellow cast in the previously gray aerial mycelium. On yeast extract-malt extract agar Pfizer F.D. 23604 had yellow spots of growth in the gray mycelium.

Melanin formation — no melanin was produced by either culture on peptone-iron agar.

Carbon utilization — (method of Pridham and Gottlieb, J. Bact., 56:107–114, 1948), Pfizer F.D. 23604 utilized glucose, L-arabinose, dextrin, D-fructose, D(+) galactose, glycerol, inositol, inulin, lactose, maltose, D-mannitol, salicin, raffinose, rhamnose, sodium acetate, D-sorbitol, sorbose, starch, sucrose, trehalose and D-xylose; dulcitol was not utilized. These results are consistent with those reported for strains of *S. hygroscopicus* in Applied Microbiology, 15:637–639, 1967 and the CBS strain of *S. hygroscopicus* reported in Industrial Microbiology, 10:183–221, 1969 with the exception that the CBS strain did not utilize inositol.

$H_2S$ production — a positive result was obtained for both cultures on peptone-iron agar slants with lead acetate strips.

Milk — like results were obtained for both cultures; no coagulation, hydrolysis complete or nearly so in 12 days; tan, soluble pigment.

Gelatin — cultures were alike in growth, color and moderate rate of liquefaction.

Special characteristics — The CBS strain of *S. hygroscopicus* developed black hygroscopic areas in three weeks on glucose-asparagine agar, oatmeal agar and yeast extract-malt extract agar whereas Pfizer F.D. 23604 showed black spots only on yeast extract-malt extract agar. Further incubation for a week and storage of some Petri dish cultures at 4°–10° C. for a fourth week increased the blackening of Pfizer F.D. 23604. On oatmeal agar, Czapek-sucrose and yeast extract-malt extract agar Pfizer F.D. 23604 produced an odor like wild onion or garlic with some earthy odor whereas *S.*

*hygroscopicus* CBS produced only the earthy odor, and this species is not described elsewhere as having the odor of wild onion. Pfizer F.D. 23604 strain of *S. hygroscopicus* produces Compound 38,295, a new polycyclic ether antibiotic, whereas *S. hygroscopicus* CBS does not, nor has the production of this antibiotic been reported for other strains of *S. hygroscopicus*.

This culture (F.D. 23604) has been deposited in The American Type Culture Collection, Rockville, Md., and designated in the collection as ATCC 31050.

Cultivation of *Streptomyces hygroscopicus* ATCC 31050 preferably takes place in aqueous nutrient media at a temperature of 28°–36° C., and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintained by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks, or alternatively, the inoculum tanks may be seeded from the shake flasks. Growth in shaken flasks will generally have reached its maximum in 3 to 5 days whereas inoculum in submerged inoculum tanks will usually be at the most favorable period in 2 to 3 days. Substantial antibiotic activity is obtained in the final fermentor stage in approximately 3 to 5 days. The antibiotic levels range from 50 to 500 mg per liter.

The process of antibiotic production is conveniently followed during fermentation by biological assay of the broth employing a sensitive strain of *Staphylococcus aureus* or *Bacillus subtilis*. Standard plate assay technique is employed in which the zone of inhibition surrounding a filter paper disc saturated with the broth is used as a measure of antibiotic potency.

Thin layer chromatography employing silica gel is a useful tool for analyzing the antibiotic produced in fermentation media and the composition of crude and purified materials extracted from the fermentation broths. The thin layer chromatograms, after development with ethyl acetate, are sprayed with 3% vanillin in ethanolic sulfuric acid (98.5:1.5%, v/v) followed by heating at 60°–80° C. for a few minutes. The antibiotic is observed as a brilliant, pinkish-red spot on a white background.

Antibiotic Compound 38,295 may be separated and recovered from clarified fermentation broth by extracting with an organic solvent such as chloroform, ethyl acetate or methyl isobutyl ketone. The major portion of the antibiotic is contained in the separated mycelium, and is conveniently extracted therefrom by slurrying the mycelium with a water-soluble solvent such as methanol.

The preferred method of separation and recovery of antibiotic Compound 38,295 is as follows: The whole (unfiltered) fermentation broth is twice extracted with about 1/5 to ¼ volume of methyl isobutyl ketone. The solvent extract is concentrated under vacuum to an oily residue which is then slurried in chloroform:hexane (1:1) and added to a silica gel column (preferably a bed of silica gel 60 topped with a layer of silica gel $PF_{254}$, both available from E. Merck, Darmstadt, Germany). The silica gel column is successively developed with hexane, chloroform:hexane (1:1) and chloroform. The main antibiotic fraction is eluted with ethyl acetate. The eluate is concentrated under vacuum, taken up in acetone and stirred for about 30–60 minutes with activated charcoal (Darco G 60). The charcoal is removed by filtration, the solution concentrated to a small volume under vacuum, a small amount of water added and the pH adjusted with sodium hydroxide to 8.0–8.5. The crystalline material that separates is removed by filtration, washed with water and dried.

The antibiotic that is isolated at this stage is a mixed sodium and potassium salt of Compound 38,295 formed with both sodium and potassium ions occurring in and scavenged from the fermentation broth and the added sodium hydroxide. Thin layer chromatograms of this material may disclose trace amounts of at least two other more polar antibiotics which like Compound 38,295 give a characteristic pinkish-red spot on graying with vanillin in ethanolic sulfuric acid.

Compound 38,295 may be obtained as a single entity by column chromatography on silica gel $PF_{254}$ made up in hexane. The mixed sodium and potassium salts are added as a solution in ethyl acetate or chloroform and the column developed under 80 p.s.i. with hexane containing increasing amounts of ethyl acetate. The progress of the separation is followed by thin layer chromatography. The appropriate fractions are combined, evaporated under vacuum and the antibiotic crystallized from acetone-water.

The free acid of Compound 38,295 may be derived from the mixed sodium/potassium salt by adjusting the pH of an ethyl acetate or chloroform solution to 4.5 with dilute phosphoric acid. The organic layer is dried over anhydrous sodium sulfate, evaporated under vacuum and the residue crystallized from chloroform-hexane.

The sodium salt of Compound 38,295 may be obtained by adjusting an ethyl acetate or chloroform solution of the free acid to pH 8.5 with sodium hydroxide (1 N). The material is crystallized from acetone-water. The crystalline potassium salt is similarly obtained using potassium hydroxide in place of NaOH.

A crystalline silver salt may be prepared by the addition of aqueous silver nitrate to an ethanolic solution of the mixed sodium/potassium salt of Compound 38,295. Other readily obtainable compounds are the copper, zinc, ammonium, calcium, magnesium and lithium salts of Compound 38,295.

Because of its end use for the prevention and treatment of coccidiosis in poultry, whole fermentation broth containing Compound 38,295 may be taken to dryness (preferably by spray-drying) and incorporated in poultry feed at the desired antibiotic potency level.

Compound 38,295 exhibits inhibitory action against the growth of a number of microorganisms (Table I). The test organism is inoculated in a series of test tubes containing nutrient medium and various concentrations of Compound 38,295 to determine the minimal concentration of the antibiotic in mcg/ml which inhibits the growth of the organism over a period of 24 hours.

Table I

| Organism | | Compound 38,295 (mixed Na/K salt) | Compound 38,295 (free acid) |
|---|---|---|---|
| Staph. aureus | 01A005 | 0.78 | 0.39 |
| | 01A052 | 0.78 | 3.12 |
| | 01A109 | 0.78 | 0.78 |
| | 01A110 | 0.39 | 1.56 |
| | 01A400 | 0.39 | 1.56 |
| Strep. faecalis | | 0.20 | 1.56 |
| Strep. pyogenes | | <0.10 | <0.10 |
| Neisseria sicca | | <0.10 | <0.10 |
| Bacillus subtilis | | <0.10 | <0.10 |
| Lactobacillus casei var casei | | 1.56 | — |
| Lactobacillus catenaforme | | 0.78 | — |
| Clostridium innocuum | | 0.20 | — |
| Clostridium bifermentans | | 0.78 | — |
| Treponema hyodysenteriae | | 0.39 | — |

Compound 38,295 and its salts exhibit excellent activity against coccidiosis infections in poultry. When incorporated in the diet of chickens at a level of 15 to 250 ppm, the compounds are effective in controlling single infections of *Eimeria tenella, E. acervulina, E. maxima* etc. and mixed infections of these organisms.

Efficacy data for Compound 38,295 and its salts against coccidiosis infections in chickens are obtained in the following manner: Groups of 3–5 ten day old SPF white leghorn cockerel chicks are fed a mash diet containing Compound 38,295 or one of its salts uniformly dispersed therein. After being on this ration for about 24 hours, each chick is inoculated per os with oocysts of the particular species of *Eimeria* being tested. Other groups of chicks fed on an antibiotic-free mash diet are similarly infected and serve as infected controls. Non-infected, non-medicated chicks serve as normal controls. The results of treatment are evaluated after 5 days in the case of *E. acervulina*, and 6 days for all other *Eimeria* species.

Table II illustrates the results obtained with the mixed sodium and potassium salt of Compound 38,295.

Table II

| Species infection | Dose (ppm) | Ave. degree of infection* | Ratio* |
|---|---|---|---|
| Eimeria tenella | 250 | 0.0 | 0.0 |
| | 125 | 0.0 | 0.0 |
| | 60 | 0.7 | 0.21 |
| | 30 | 1.7 | 0.54 |
| | 15 | 2.7 | 0.86 |
| Eimeria acervulina | 250 | 0.0 | 0.0 |
| | 125 | 0.2 | 0.1 |
| | 60 | 0.0 | 0.0 |
| | 45 | 0.4 | 0.2 |
| | 30 | 1.2 | 0.6 |
| | 15 | 2.0 | 1.0 |
| Eimeria necatrix | 250 | 0.0 | 0.0 |
| | 125 | 0.2 | 0.13 |
| | 60 | 0.2 | 0.13 |
| Eimeria maxima | 250 | 0.0 | 0.0 |
| | 125 | 0.0 | 0.0 |
| | 60 | 0.4 | 0.25 |
| | 45 | 0.6 | 0.33 |
| | 30 | 0.8 | 0.44 |
| | 15 | 1.8 | 0.66 |
| Eimeria brunetti | 250 | 0.4 | 0.22 |
| | 125 | 0.4 | 0.22 |
| | 60 | 0.8 | 0.44 |
| | 45 | 1.2 | 0.66 |
| | 30 | 1.6 | 0.88 |
| | 15 | 1.6 | 0.88 |
| Mixed infection (Coccivac D, Sterwine Laboratories, Opelika, Alabama) | 250 | 0.0, 0.0** | 0.0, 0.0 |
| | 125 | 0.2, 0.4 | 0.08, 0.18 |
| | 60 | 0.2, 0.0 | 0.08, 0.0 |
| | 50 | 1.0, 0.6 | 0.38, 0.21 |
| | 40 | 1.2, 1.0 | 0.46, 0.35 |
| | 30 | 2.6, 2.0 | 0.85, 0.71 |

*The criteria used to measure anticoccidial activity consist of lesion scores of 0 to 4 for *E. tenella* (J.E. Lynch, Am J. Vet. Res. 22:324–326, 1961) and 0 to 3 for other species (J. Johnson and W.H. Reid, Exp. Parasit., 28:30–36, 1970). A constant ratio is established by dividing the lesion score of each treated group by the lesion score of the infected control.
**The first number pertains to intestinal lesions and the second number to cecal lesions.

Similar results may be obtained with the free acid, sodium salt, potassium salt or dried fermentation medium containing Compound 38,295 in the ration at the desired antibiotic potency level.

The growth promotant properties of Compound 38,295 are illustrated by the following trials with cattle.

Angus heifer calves are randomly assigned to pens, 5 calves per pen, and administered Compound 38,295 orally by bolus, in drinking water, etc. However, the compound is advantageously and expeditiously administered, on an activity basis, by incorporation into feed compositions high in roughage at levels of 11 to 33 ppm. Compound 38,295 may be in such various forms as the free acid, sodium salt, potassium salt, mixed sodium and potassium salts or dried fermentation broth produced by *Streptomyces hygroscopicus* ATCC 31050.

Non-medicated and Compound 38,295 feed compositions are administered to the test animals ad libitum. The feed composition is a 12.5% protein - 75:25 conc:roughage cattle finisher ration containing corn, soybean meal, alfalfa meal, calcium phosphate, molasses, vitamins and trace minerals. Compound 38,295 is contained in a premix along with ground corn, minerals and vitamins.

| BASAL RATION (12.5% Protein - 75:25 Conc:Roughage Cattle Finisher Ration) | |
|---|---|
| Ingredient | Percent |
| Ground yellow corn | 55.6 |
| Soybean meal, 48% protein | 6.3 |
| Alfalfa meal, 17% protein | 25.0 |
| Dried molasses* | 10.0 |
| Soybean oil | 2.0 |
| Dicalcium phosphate (24% Ca, 18.5% P) | 0.40 |
| Trace mineral salt** | 0.50 |
| Vitamin-mineral premix*** | 0.20 |

*Cane molasses on a corn-cob fraction carrier: not less than 3% crude protein, not more than 15% fiber, not less than 42% inert sugar, maximum of 6% water.
**Contributed the following levels of trace minerals in parts per million: manganese 10; iron 6.25; copper 1.25; iodine 0.025; cobalt 0.86; zinc 45.
***Contributed the following levels of vitamins per pound of ration: vitamin A 1497 I.U.; vitamin D 200 I.U.; vitamin E 25 I.U.

| PREMIX | |
|---|---|
| Ingredient | Amount (4 lbs.) |
| Vitamin A Supplement (30,000 IU/gm) | 0.22 lb. |
| Vitamin $D_3$ Supplement (200,000 IU/gm) | 2.00 gm. |
| Vitamin Supplement (125,000 IU/lb.) | 0.40 lb. |
| Zinc Oxide (79.4% zinc) | 38.0 gm. |
| Cobaltous Carbonate (45% cobalt) | 1.70 gm. |
| Soymill run or finely ground corn | 3.27 lb. |
| Compound 38,295 | 40.0 gm. |

A pound of premix per ton of complete ration gives a final Compound 38,295 level of 11 ppm.

Table III illustrates the results of a 28 day test obtained with three replicate pens of 5 calves per pen, approximate initial weight of 400 lbs. per calf.

Table III (mixed sodium and potassium salts of Compound 38,295)

| Treatment (ppm) | ADG* | | ADF | | Feed/Gain* | |
|---|---|---|---|---|---|---|
| | lbs. | Index | lbs. | Index | Ratio | Index |
| Control | 2.07 | 100.0 | 14.2 | 100.0 | 6.95 | 100.0 |
| Compound 38,295 (11) | 2.29 | 110.6 | 13.5 | 95.1 | 5.94 | 117.0 |
| Compound 38,295 (33) | 2.42 | 116.9 | 12.4 | 87.3 | 5.11 | 136.0 |

*average daily gain
**average daily feed
***lbs. of feed per lb. of gain

Substantially the same results may be obtained with the free acid, sodium salt, potassium salt or dried fermentation broth containing Compound 38,295.

Comparable results may be obtained with other ruminants such as sheep or monogastric animals such as horses, pigs and rabbits.

EXAMPLE I

A sterile aqueous medium having the following composition is prepared:

| | Grams/liter |
|---|---|
| Glucose | 10.0 |
| Soluble starch | 20.0 |
| Yeast extract | 5.0 |
| Enzymatic digest of casein | 5.0 |
| Meat meal | 5.0 |
| CaCO$_3$ | 1.0 |
| pH - 7.0 | |

Cells from a slant of *Streptomyces hygroscopicus* ATCC 31050 are transferred to a series of 300 ml flasks each containing 50 ml of this sterile medium and shaken on a rotary shaker for 3-4 days at 28°-30° C. Five ml aliquots of this grown inoculum are transferred aseptically to 300 ml flasks containing 100 ml of sterile medium as described above. After shaking for 3-4 days at 28°-30° C., the grown inoculum is transferred to four-liter fermentors containing two liters of the following sterile medium:

| | Grams/liter |
|---|---|
| Glucose | 10.0 |
| Corn starch | 10.0 |
| Soy flour | 10.0 |
| Grain solubles | 5.0 |
| NaCl | 5.0 |
| CaCO$_3$ | 1.0 |
| pH - 6.6 | |

The fermentation is conducted for 90-120 hours at 28°-36° C. with stirring at 1700 revolutions per minute and aeration at about one volume of air per volume of broth per minute. Large fermentors containing from 80 to 10,000 gallons of medium may be inoculated with about 2% of this growth. The fermentation is conducted until an antibiotic potency of at least 50 mg per liter is obtained (90 to 120 hours).

One hundred liters of whole, unfiltered fermentation broth are twice extracted with one-fifth volume of methyl isobutyl ketone. The separated solvent extract is concentrated in vacuo to an oily residue (769 g) which is dispersed on silica gel by its addition in solution in 2 liters of chloroform to 1 kilogram of silica gel PF$_{254}$, followed by removal of the solvent under vacuum. The resultant residue is slurried in 2 liters of chloroform:hexane (1:1) and added to a bed of 300 grams of silica gel 60 topped with a layer of 300 grams of silica gel PF$_{254}$. The silica gel is then washed successively with 2 gallons of hexane, 2 gallons of chloroform:hexane (1:1) and 2 gallons of chloroform. The antibiotic is eluted with 1 gallon of ethyl acetate. The ethyl acetate is removed under vacuum and the residue (38 g) is dissolved in 400 ml of acetone. The acetone solution is stirred at room temperature for about 45 minutes with about 40 g of activated charcoal (Darco G 60). Filtration is followed by concentration to approximately 200 ml and dilution with 100 ml of water. Compound 38,295 separates as the mixed sodium/potassium salt on adjustment of the pH to 8.5 with 1.0 N NaOH. The crystalline material (13.8 g) is dissolved in ethyl acetate and chromatographed on a column of silica gel PF$_{254}$ made up in hexane. The column is developed under 80 p.s.i. with hexane containing increasing amounts of ethyl acetate. The progress of the separation is followed by thin layer chromatography. The appropriate fractions are combined, evaporated under vacuum and the pure compound crystallized from acetone-water.

The pure, crystalline mixed sodium/potassium salt of Compound 38,295 has a melting point of 200° C. and an optical rotation of $[\alpha]_D^{25} = +36°$ at a concentration of 1% in methanol. After drying in vacuo overnight at 70° C. over phosphorus pentoxide, the average analysis for carbon is 60.58%, and hydrogen is 8.56%.

The compound is soluble in methanol, ethanol, acetone, chloroform, methylene chloride, diethyl ether, ethyl acetate and methyl isobutyl ketone; partially soluble in hexane; and insoluble in water.

The mixed sodium/potassium salt of Compound 38,295 possesses no characteristic ultraviolet light absorption pattern.

The infrared spectrum of the mixed sodium/potassium salt, FIG. 1, is attached. A KBr pellet shows characteristic absorption in the infrared region at the following wavelengths in microns: 2.92, 3.40, 6.27, 6.85, 7.22, 8.40, 9.00, 9.15, 9.25, 9.48, 9.98, 10.45, 10.68 and 11.45.

EXAMPLE II

The method of Example I may be repeated employing clarified fermentation broth in place of whole unfiltered fermentation broth.

EXAMPLE III

The mycelium separated from the clarified fermentation broth of Example II is slurried several times with methanol, the methanol extract concentrated under vacuum and the residue treated by the method of Example I.

EXAMPLE IV

The fermentation process of the method of Example I is repeated employing a fermentation medium of the following composition:

| | Grams/liter |
|---|---|
| Glucose | 20.0 |
| Corn starch | 10.0 |
| Soy flour | 10.0 |
| Grain solubles | 5.0 |
| Fe$_2$(SO$_4$)$_3$ | 0.2 |
| MnCl$_2$ | 0.2 |
| CaCO$_3$ | 1.0 |
| NaCl | 5.0 |
| Methyl oleate | 2.0 |
| Soybean oil | 2.0 |
| pH 6.6-6.7 | |

At the end of the fermentation cycle, the whole unfiltered fermentation broth is taken to dryness by spray-drying.

EXAMPLE V

The mixed sodium/potassium salt of Compound 38,295 is dissolved in ethyl acetate and the pH adjusted to 4.5 with dilute phosphoric acid. The solvent layer is dried over anhydrous sodium sulfate, evaporated in vacuo and the residue crystallized from chloroform-hexane to yield the crystalline acid which has a melting point of 135°–138° C. and an optical rotation of $[\alpha]_D^{25} = +38°$ at a concentration of 1% in methanol. After drying overnight in vacuo at 70° C. over phosphorus pentoxide, the average composition by weight is 61.65% carbon, 8.94% hydrogen and 29.41% oxygen (by difference). The free acid of Compound 38,295 possesses no characteristic ultraviolet light absorption pattern.

The infrared spectrum of the free acid of Compound 38,295, FIG. 2, is attached. A KBr pellet shows characteristic absorption in the infrared region at the following wavelengths in microns: 2.92, 3.43, 5.74, 6.85, 7.25, 7.53, 8.28, 8.60, 8.80, 9.00, 9.15, 9.80, 10.10, 10.45, 10.68, 10.92 and 11.13.

X-ray crystal analysis of the silver salt of Compound 38,295 established the structural formula of the following representation:

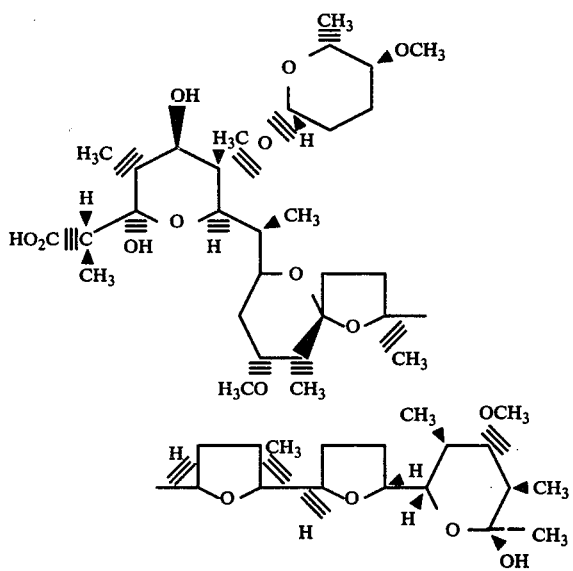

EXAMPLE VI

The sodium salt of Compound 38,295 is obtained by the addition of 1.0 N NaOH to a pH of 8.5 to an ethyl acetate solution of the free acid of Example V. The material crystallized from acetone-water has a melting point of 197°–198° C. and an optical rotation of $[\alpha]_D^{25} = +38°$ at a concentration of 1.03% in methanol. After drying in vacuo overnight at 70° C. over phosphorus pentoxide, the sodium salt analyzes for 60.28% carbon and 8.76% hydrogen.

The infrared spectrum of the sodium salt of Compound 38,295, FIG. 3, is attached. A KBr pellet shows characteristic absorption in the infrared region at the following wavelengths in microns: 2.94, 3.40, 6.25, 6.85, 7.20, 7.45, 8.38, 9.00, 9.27, 9.48, 10.00, 10.45, 10.65, 10.90, 11.13 and 11.47.

EXAMPLE VII

The potassium salt of Compound 38,295 is prepared by the method of Example VI employing potassium hydroxide in place of sodium hydroxide. The material crystallized from acetone-water has a melting point of 196°–198° C. and an optical rotation of $[\alpha]_D^{25} = +38°$ at a concentration of 1.02% in methanol. After drying in vacuo overnight at 70° C. over phosphorus pentoxide, the compound analyzes for 60.58% carbon and 8.70% hydrogen.

The infrared spectrum of the potassium salt of Compound 38,925, FIG. 4, is attached. A KBr pellet shows characteristic absorption in the infrared region at the following wavelengths in microns: 2.94, 3.42, 6.27, 6.84, 7.20, 8.75, 9.00, 9.14, 9.30, 9.45, 10.45, 10.92, 11.15 and 11.47.

EXAMPLE VIII

The silver salt of Compound 38,295 is prepared by the addition of aqueous silver nitrate to an ethanolic solution of the mixed sodium/potassium salt of Example I. The solid that separates is crystallized from methanol. It has a melting point of 198°–200° C. and an optical rotation of $[\alpha]_D^{25} = +27°$ at a concentration of 0.982% in methanol. The average composition of a sample dried overnight in vacuo at 70° C. over phosphorus pentoxide is 55.95% carbon and 7.89% hydrogen. The molecular weight of the crystalline silver salt of Compound 38,295, determined from X-ray data, is 1060 ± 4 atomic mass units.

What is claimed is:

1. Compound 38,295, an antibiotic having the formula

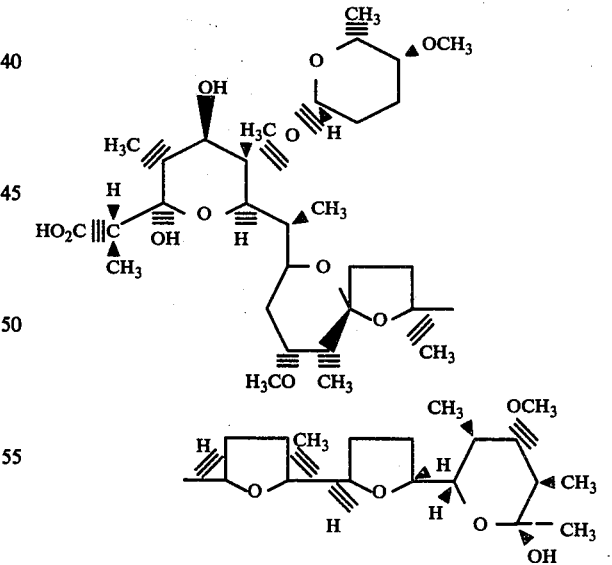

and the cationic salts thereof.

2. The compound of claim 1 wherein the cationic salt is the sodium salt.

3. The compound of claim 1 wherein the cationic salt is the potassium salt.

4. The compound of claim 1 wherein the cationic salt is the mixed sodium and potassium salt.

* * * * *